US008551765B2

(12) United States Patent
Okamura et al.

(10) Patent No.: US 8,551,765 B2
(45) Date of Patent: *Oct. 8, 2013

(54) SOLID SUPPORT HAVING ELECTROSTATIC LAYER AND USE THEREOF

(75) Inventors: Hiroshi Okamura, Kudamatsu (JP); Michifumi Tanga, Kudamatsu (JP); Hirofumi Yamano, Kudamatsu (JP); Mitsuyoshi Ohba, Kudamatsu (JP)

(73) Assignee: Toyo Kohan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/521,176

(22) PCT Filed: Jul. 3, 2003

(86) PCT No.: PCT/JP03/08488
§ 371 (c)(1),
(2), (4) Date: Jan. 14, 2005

(87) PCT Pub. No.: WO2004/007710
PCT Pub. Date: Jan. 22, 2004

(65) Prior Publication Data
US 2006/0204959 A1  Sep. 14, 2006

(30) Foreign Application Priority Data

Jul. 17, 2002 (JP) ................................. 2002-207886
Sep. 20, 2002 (JP) ................................. 2002-275797

(51) Int. Cl.
*C12M 1/38* (2006.01)
*C12M 3/00* (2006.01)
*C12Q 1/68* (2006.01)
*C23C 16/00* (2006.01)
*B05D 1/36* (2006.01)
*C07H 21/02* (2006.01)
*C07H 21/04* (2006.01)

(52) U.S. Cl.
USPC ... 435/287.2; 435/6.1; 435/287.8; 427/249.8; 427/255.14; 427/402; 536/23.1; 536/24.3

(58) Field of Classification Search
USPC ............. 435/6.1, 287.2, 287.8; 427/249.8, 427/255.14, 402; 536/23.1, 24.3
See application file for complete search history.

(56) References Cited

U.S. PATENT DOCUMENTS

| 5,688,642 | A | * | 11/1997 | Chrisey et al. ............... 435/6 |
| 5,929,194 | A | * | 7/1999 | Woo et al. ................. 528/229 |
| 6,066,461 | A |   | 5/2000 | McMillian et al. |
| 6,162,605 | A |   | 12/2000 | Fort et al. |
| 6,531,302 | B1 |   | 3/2003 | Nerenberg et al. |
| 6,858,392 | B2 | * | 2/2005 | Iwaki et al. ................. 435/6 |
| 6,911,535 | B2 | * | 6/2005 | Schwartz .................. 530/402 |
| 6,916,541 | B2 | * | 7/2005 | Pantano et al. ............. 428/429 |
| 2002/0146504 | A1 |   | 10/2002 | Schwartz |
| 2002/0197417 | A1 | * | 12/2002 | Nakamura et al. ........... 427/585 |
| 2003/0008413 | A1 | * | 1/2003 | Kim et al. ................. 436/518 |
| 2003/0124332 | A1 | * | 7/2003 | Mao et al. ................. 428/304.4 |

FOREIGN PATENT DOCUMENTS

| EP | 1063286 | * | 12/2000 |
| JP | EP 1215287 | * | 6/2002 |
| WO | WO 01/02538 | * | 1/2001 |
| WO | WO/01/66244 | * | 9/2001 |
| WO | WO 03/020425 | * | 3/2003 |

OTHER PUBLICATIONS

Langer et al, Thermal conductivity of thin metallic films measured by photothermal profile analysis, 1997, Rev. Sci. Instrum. 68, 1510-1513.*
Consolandi et al, Two efficient polymeric chemical platforms for oligonucleotide microarray preparation, 2002, Nucleosides, Nucleotides and Nucleic Acids, 21, 561-580.*
Bertrand et al, Ultrathin polymer coatings by complexation of polyelectrolytes at interfaces:suitable materials, structure and properties, 2000, Macromol. Rapid Commun. 21, 319-348.*
Jordan et al, Surface plasmon resonance imaging measurements of DNA hybridization adsorption and streptavidin/DNA multilayer formation at chemically modified surfaces, 1997, Anal. Chem., 69, 4939-4947.*
White, Evaluation of layer by layer of polyelectrolyte multilayers in cell patterning technology, Jun. 2002, MIT thesis, pp. 1-49, publication date Jun. 17, 2002.*
White, Evaluation of Layer-by-Layer Assembly of Polyelectrolyte Multilayers in Cell Patterning Technology, 2002, Thesis, Massachusetts Institute of Technology, Thesis, pp. 1-49.*
Huber et al, Detection of Single Base Alterations in Genomic DNA by Solid Phase Polymerase Chain Reaction on Oligonucleotide Microarrays, 2001, Analytical Biochemistry 299, 24±30.*
Flink et al, Functionalization of self assembled monolayers on glass and oxidized silicon wafers by surface reactions, 2001, J. Phys. Org. Chem., 14, 407-415.*
Tadashi Matsunaga et al., DNA Chip Oyo Gijutsu, Kabushiki Kaisha CMC, 55-66 (2000).

* cited by examiner

*Primary Examiner* — Narayan Bhat
(74) *Attorney, Agent, or Firm* — Browdy and Neimark, PLLC

(57) ABSTRACT

It is intended to provide a solid support capable of immobilizing nucleic acid molecules in a high proportion, and with a high bond strength to nucleic acid molecules. The solid support comprises a substrate and, provided thereon, an electrostatic layer for electrostatically attracting nucleic acid molecules and functional groups capable of covalently binding to nucleic acid molecules.

10 Claims, No Drawings

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
gatgagttgt gtccgtacaa ct                    22

<210> SEQ ID NO 2
<211> LENGTH: 25
<212> TYPE: DNA
<213> ORGANISM: Artificial Sequence

```
<220> FEATURE:
<223> OTHER INFORMATION: Synthetic

<400> SEQUENCE: 2
ggttatcgaa atcagccaca gcgcc                                              25
```

SOLID SUPPORT HAVING ELECTROSTATIC LAYER AND USE THEREOF

TECHNICAL FIELD

The present invention relates to a support for immobilizing DNA or the like and an immobilized nucleic acid molecule.

BACKGROUND ART

Conventionally, in JP-A-7-75544 and JP-A-7-303469, polymerase chain reaction (PCR) is reported as a method of synthesizing a nucleotide sequence from an existing sequence.

The polymerase chain reaction (PCR) is a method in which a target DNA is flanked by a pair of primers, a DNA polymerase is allowed to act on it repeatedly, whereby the region flanked by the primers can be continuously amplified.

By PCR, only the target sequence can be substantially correctly amplified to produce a large number of copies, further an efficient amplification is possible in a short time, therefore, PCR is widely used for a variety of studies, assays, tests and the like in biochemical, medical fields, etc., at present.

It has been conventionally assumed that the principle of PCR is to control temperature, and the reaction is performed by repeating heating and cooling procedures (thermal cycle). More specifically, for example, by denaturing a double-stranded DNA molecule, which is the target for amplification, into complementary single strands at a high temperature, annealing a primer, which has been selected to be complementary to a part of the DNA, to the strand by cooling, and extending the DNA to the downstream of the primer with a DNA polymerase by heating again, and so on, one cycle consisting of the steps of denaturing, annealing and extending is repeated multiple times, whereby a large amount of double-stranded DNA can be amplified.

Specifically, it is necessary to repeat the thermal cycle, which consists of 1) raising the temperature of a sample to 95° C. in order to disrupt the hydrogen bond of the double-stranded DNA, 2) subsequently, lowering the temperature of the sample to 45° C. in order to recombine the DNA to a primer for replication, 3) further, raising the temperature of the sample to 74° C. in order to replicate the DNA by extending the primer with a heat-resistant polymerase, a number of times. In such a DNA amplification reaction, the foregoing thermal cycle was carried out by putting a sample into a container made of synthetic resin or the like, and accommodating this container into an aluminum block.

However, the foregoing thermal cycle consumed a lot of time, and it took several hours to obtain a required amount of DNA. In addition, when reaction is carried out by controlling the temperature (heating and cooling), there is a limit on changing the temperature in an instant, and changeover of each step cannot be performed smoothly, whereby the accuracy of the nucleotide sequence to be amplified may be affected, or DNA other than the target may be replicated in some cases. Further, in order to change the temperature rapidly, a special apparatus or technique is needed, therefore there are an economic problem such as investment in equipment and a technical problem.

In view of the foregoing problems, as a support capable of easily immobilizing DNA and suitable for replicating DNA by DNA amplification reaction, in WO 00/22108, WO 02/12891 or JP-A-2002-82116, a solid support which comprises, on the surface of a substrate, a surface-treated layer and chemically modified layer having a functional group capable of covalently binding to a nucleic acid molecule sequentially has been developed.

However, the amount of DNA immobilized on the foregoing solid support and the bond strength to DNA are not always sufficient, therefore, the emergence of a solid support capable of immobilizing DNA in a higher proportion and with a higher bond strength to DNA has been awaited.

The object of the present invention is to provide a solid support capable of immobilizing nucleic acid molecules in a higher proportion, and with a higher bond strength to nucleic acid molecules.

DISCLOSURE OF THE INVENTION

The present inventors carried out intensive studies in order to solve the foregoing problems, and as a result, found out that the immobilized amount of nucleic acid molecules and the bond strength to nucleic acid molecules are significantly improved by further providing an electrostatic layer for electrostatically attracting nucleic acid molecules on a solid support having a functional group capable of covalently binding to a nucleic acid molecule on a substrate, thereby accomplishing the present invention.

More specifically, the present invention includes the following inventions.

(1) A solid support having an electrostatic layer for electrostatically attracting a nucleic acid molecule and a functional group capable of covalently binding to a nucleic acid molecule on a substrate.

(2) The solid support according to the foregoing (1), in which the surface of the substrate is surface-treated with at least one kind selected from diamond, a soft diamond, a carbonaceous matter and carbide.

(3) The solid support according to the foregoing (1) or (2), in which the electrostatic layer comprises an amino group-containing compound which does not covalently bind to the substrate.

(4) The solid support according to the foregoing (1) or (2), in which the electrostatic layer is composed of an amino group-containing compound which covalently binds to the substrate and the amino group-containing compound has an amino group at the terminus to which the substrate does not bind.

(5) The solid support according to any one of the foreging (1) to (3), which is obtained by depositing a compound having an unsubstituted or monosubstituted amino group and a carbon compound on the substrate and then introducing a functional group capable of covalently binding to a nucleic acid molecule.

(6) The solid support according to any one of the foregoing (1) to (4), which is obtained by dipping the substrate in a solution containing a compound having an unsubstituted or monosubstituted amino group and then introducing a functional group capable of covalently binding to a nucleic acid molecule.

(7) The solid support according to the foregoing (6), in which the compound having an unsubstituted or monosubstituted amino group is polyarylamine.

(8) The solid support according to any one of the foregoing (1) to (7), in which the nucleic acid molecule is DNA.

(9) An immobilized nucleic acid molecule, which comprises a nucleic acid molecule immobilized on a solid support according to any one of the foregoing (1) to (8).

(10) A method of producing a solid support characterized by depositing a compound having an unsubstituted or monosubstituted amino group and a carbon compound on the substrate and then introducing a functional group capable of covalently binding to a nucleic acid molecule.

(11) A method of producing a solid support characterized by dipping the substrate in a solution containing a compound having an unsubstituted or monosubstituted amino group and then introducing a functional group capable of covalently binding to a nucleic acid molecule.

(12) A method of immobilizing a primer on a solid support according to any one of (1) to (8), and hybridizing a nucleic acid molecule to the primer, thereby extending a nucleic acid molecule complementary to the nucleic acid molecule.

(13) A method of detecting a nucleic acid molecule, which comprises immobilizing a primer on a solid support according to any one of (1) to (8), hybridizing a nucleic acid molecule to the primer, extending a nucleic acid molecule complementary to the nucleic acid molecule in the presence of a labeled nucleic acid and reading a signal derived from the labeled nucleic acid incorporated into the complementary nucleic acid molecule.

(14) A method of amplifying a nucleic acid molecule by immobilizing a primer on a solid support according to any one of (1) to (8), hybridizing a nucleic acid molecule to the primer and subjecting it to PCR reaction.

(15) A method of amplifying DNA by immobilizing a primer on a solid support according to any one of (1) to (8), hybridizing DNA to the primer and performing reaction with a strand-displacing DNA polymerase.

(16) The method according to (13), which further comprises the step of amplifying the nucleic acid molecule after hybridizing a nucleic acid molecule to the primer.

BEST MODE FOR CARRYING OUT THE INVENTION

Examples of a material of the substrate to be used in the present invention include, for example, silicone, glass, fiber, wood, paper, ceramics, and plastic (e.g., polyester resin, polyethylene resin, polypropylene resin, ABS resin (acrylonitrile butadiene styrene resin), nylon, acrylic resin, fluorocarbon resin, polycarbonate resin, polyurethane resin, methylpentene resin, phenolic resin, melamine resin, epoxy resin, polyvinyl chloride resin).

In the case where the foregoing members are used as the material of the substrate, a surface-treated layer may not be provided, however, it is more preferred that surface treatment be carried out in order to firmly immobilize a compound for introducing a functional group capable of covalently binding to a nucleic acid molecule on the substrate.

For the surface treatment, it is preferred to use any of synthetic diamond, high-pressure synthetic diamond, natural diamond, a soft diamond (e.g., a diamond-like carbon), amorphous carbon, a carbonaceous matter (e.g., graphite, fullerene or carbon nanotube), a mixture thereof, or a laminated product thereof. In addition, carbide such as hafnium carbide, niobium carbide, silicon carbide, tantalum carbide, thorium carbide, titanium carbide, uranium carbide, tungsten carbide, zirconium carbide, molybdenum carbide, chromium carbide or vanadium carbide may be used. The term of soft diamond here is used as a collective term of a partial diamond structure, which is a mixture of diamond and carbon, such as, so-called a diamond-like carbon (DLC), and the mixing ratio thereof is not particularly limited.

As one example of the surface-treated substrate, a substrate in which a film has been formed with a soft diamond on a slide glass is exemplified. It is preferred that such a substrate be produced by the ionization deposition method in a mixed gas containing 0 to 99% by volume of hydrogen gas and the balance of methane gas (100 to 1% by volume) with a diamond-like carbon.

It is preferred that the thickness of the surface-treated layer be 1 nm to 100 μm.

The formation of the surface-treated layer on the substrate can be carried out by a known method such as the microwave plasma CVD (chemical vapor deposition) method, ECRCVD (electric cyclotron resonance chemical vapor deposition) method, IPC (inductive coupled plasma) method, DC sputtering method, ECR (electric cyclotron resonance) sputtering method, ion plating method, arc ion plating method, EB (electron beam) deposition method, resistance heating vapor deposition method, ionization deposition method, arc deposition method, laser deposition method.

Examples of the substrate to be used in the present invention include, not only the structure in which the surface-treated layer has been formed as described above, but also synthetic diamond, high-pressure synthetic diamond, natural diamond, a soft diamond (e.g., a diamond-like carbon), amorphous carbon; metals such as gold, silver, copper, aluminum, tungsten and molybdenum; plastic (such as polyester resin, polyethylene resin, polypropylene resin, ABS resin, nylon, acrylic resin, fluorocarbon resin, polycarbonate resin, polyurethane resin, methylpentene resin, phenolic resin, melamine resin, epoxy resin, polyvinyl chloride resin); the one formed by mixing and combining powder of the foregoing metal, powder of ceramic or the like with the foregoing resin as a binder; the one obtained by sintering at a high temperature a material such as powder of the foregoing metal or powder of ceramic, which has been powder-pressed with press-molding machine. In addition, the substrate may be a laminated product or a composite of the foregoing materials (for example, a composite of diamond and another substance, (e.g. a two-phase substance)).

The shape and the size of the substrate are not particularly limited. However, with regard to the shape, it may be in the form of plate, thread, sphere, polygon, powder and the like, and with regard to the size, in the case of using the one in the form of plate, it is generally about 0.1 to 100 mm of width, 0.1 to 100 mm of length and 0.01 to 10 mm of thickness.

In addition, on the front face or back face of the substrate, a monolayer of Ti, Au, Pt, Nb, Cr, TiC, TiN or the like, or a composite layer thereof may be formed as a reflective layer. The thickness of the reflective layer is preferably 10 nm or more, more preferably 100 nm or more, because it is necessary to be uniform throughout the surface.

In the case of using glass as the substrate, it is also preferred that the surface be intentionally roughened within the range of 1 nm to 1000 nm expressed in Ra (JIS B 0601). Such roughened surface is advantageous in that the surface area of the substrate is increased, whereby a large amount of DNA probes or the like can be immobilized at a high density.

The solid support of the present invention is provided with an electrostatic layer for electrostatically attracting a nucleic acid molecule.

The electrostatic layer is not particularly limited as long as it attracts a nucleic acid molecule electrostatically and improves the immobilized amount of nucleic acid molecules, however, it can be formed by, for example using a positively charged compound such as an amino group-containing compound.

Examples of the foregoing amino group-containing compound include a compound having an unsubstituted amino group ($-NH_2$) or an amino group, which has been monosubstituted with an alkyl group having 1 to 6 carbon atoms or the like ($-NHR$; R is a substituent), and for example, ethylenediamine, hexamethylenediamine, n-propylamine, monomethylamine, dimethylamine, monoethylamine, diethylamine, arylamine, aminoazobenzene, aminoalcohol, (e.g., ethanolamine), acrinol, aminobenzoic acid, aminoanthraquinone, amino acids (glycine, alanine, valine, leucine, serine, threonine, cysteine, methionine, phenylalanine, tryptophan, tyrosine, proline, cystine, glutamic acid, aspartic acid, glutamine, asparagine, lysine, arginine and histidine), aniline, a polymer thereof (e.g., polyallylamine and polylysine) and a copolymer thereof; a polyamine (polyvalent amine) such as 4,4',4"-triaminotriphenylmethane, triamterene, spermidine, spermin and putrescine.

The electrostatic layer may be formed without covalently binding to the substrate or the surface-treated layer, or may be formed by covalently binding to the substrate or the surface-treated layer.

In the case of forming the electrostatic layer without covalently binding to the substrate or the surface-treated layer, a carbonaceous film containing an amino group is formed by, for example, introducing the foregoing amino group-containing compound into a film-forming apparatus when the surface-treated layer is formed. As the compound to be introduced into a film-forming apparatus, ammonia gas may be used. In addition, the surface-treated layer may be a multiple layer in which a layer containing an amino group is formed after forming an adherent layer. In this case, film forming may be carried out also in an atmosphere containing ammonia gas.

Further, in the case of forming the electrostatic layer without covalently binding to the substrate or the surface-treated layer, it is preferred to introduce a functional group capable of covalently binding to a nucleic acid molecule after depositing the forgoing compound having an unsubstituted or monosubstituted amino group and a carbon compound on the substrate in order to enhance the affinity, namely adhesiveness between the electrostatic layer and the substrate or the surface-treated layer. The carbon compound to be used here is not particularly limited as long as it can be supplied as a gas, however, preferred are, for example, methane, ethane and propane that are gas at a normal temperature. As the method for deposition, the ionization deposition method is preferred. As the condition of the ionization deposition method, it is preferred that the working pressure be in the range of 0.1 to 50 Pa and the accelerating voltage be in the range of 200 to 1000 V.

In the case of forming the electrostatic layer by covalently binding to the substrate or the surface-treated layer, the electrostatic layer can be formed by, for example, irradiating the substrate or the substrate provided with the surface-treated layer with ultraviolet rays in chlorine gas to chlorinate the surface, and reacting, among the foregoing amino group-containing compounds, for example, a polyvalent amine such as polyallylamine, polylysine 4,4',4"-triaminotriphenylmethane or triamterene to introduce an amino group into the terminus to which the substrate does not bind.

Further, in the case of carrying out the reaction of introducing a functional group capable of covalently binding to a nucleic acid molecule into the substrate provided with the electrostatic layer (e.g., introduction of a carboxyl group by using a dicarboxylic acid or polyvalent carboxylic acid) in a solution, it is preferred to introduce a functional group capable of covalently binding to a nucleic acid molecule after dipping the substrate in a solution containing the foregoing compound having an unsubstituted or monosubstituted amino group. Examples of the solvent for the foregoing solution include, for example, water N-methylpyrrolidone and ethanol.

In the case of introducing a carboxyl group by using a dicarboxylic acid or polyvalent carboxylic acid into the substrate provided with the electrostatic layer, it is preferred to activate it with N-hydroxysuccinimide and/or a carbodiimide in advance, or to carry out the reaction in the presence of N-hydroxysuccinimide and/or a carbodiimide.

In the case of forming the electrostatic layer by dipping the substrate in a solution containing the compound having an unsubstituted or monosubstituted amino group, if polyallylamine is used as the amino group-containing compound, the adhesiveness to the substrate will be excellent and the immobilized amount of the nucleic acid molecule will be more improved.

It is preferred that the thickness of the electrostatic layer be 1 nm to 500 µm.

As described above, the surface of the substrate provided with the electrostatic layer is chemically modified in order to introduce a functional group capable of covalently binding to a nucleic acid molecule.

Examples of the foregoing functional group include, for example, a carboxyl group, active ester group, haloformyl group, hydroxyl group, sulfate group, cyano group, nitro group, thiol group and amino group.

Examples of the compound to be used for introducing a carboxyl group as the functional group include, for example, a halocarboxylic acid represented by the formula: $X-R^1-COOH$ (wherein X represents a halogen atom, and $R^1$ represents a divalent hydrocarbon group having 1 to 12 carbon atoms) such as chloroacetic acid, fluoroacetic acid, bromoacetic acid, iodoacetic acid, 2-chloropropionic acid, 3-chloropropionic acid, 3-chloroacrylic acid or 4-chlorobenzoic acid; a dicarboxylic acid represented by the formula: $HOOC-R^2-COOH$ (wherein $R^2$ represents a single bond or a divalent hydrocarbon group having 1 to 12 carbon atoms) such as oxalic acid, malonic acid, succinic acid, maleic acid, fumaric acid or phthalic acid; a polyvalent carboxylic acid such as polyacrylic acid, polymethacrylic acid, trimellitic acid or butanetetracarboxylic acid; a keto acid or aldehyde acid represented by the formula: $R^3-CO-R^4-COOH$ (wherein $R^3$ represents a hydrogen atom or a divalent hydrocarbon group having 1 to 12 carbon atoms and $R^4$ represents a divalent hydrocarbon group having 1 to 12 carbon atoms); a monohalide of dicarboxylic acid represented by the formula: $X-OC-R^5-COOH$ (wherein X represents a halogen atom and $R^5$ represents a single bond or a divalent hydrocarbon group having 1 to 12 carbon atoms) such as monochloride succinate or monochloride malonate; an acid anhydride such as phthalic acid anhydride, succinic acid anhydride, oxalic acid anhydride, maleic acid anhydride or butanetetracarboxylic acid anhydride.

With regard to the carboxyl group introduced as described above, active esterification thereof can be carried out with a dehydration condensing agent such as cyanamide or carbodiimide (e.g. 1-[3-(dimethylamino)propyl]-3-ethylcarbodiimide) and a compound such as N-hydroxysuccinimide.

Examples of the compound to be used for introducing a haloformyl group as the functional group include, for example, a dihalide of dicarboxylic acid represented by the formula: $X-OC-R^6-CO-X$ (wherein X represents a halogen atom, and $R^6$ represents a single bond or a divalent hydrocarbon group having 1 to 12 carbon atoms) such as chloride succinate or chloride malonate.

Examples of the compound to be used for introducing a hydroxyl group as the functional group include, for example, a hydroxy acid or phenol acid represented by the formula: $HO-R^7-COOH$ (wherein $R^7$ represents a divalent hydrocarbon group having 1 to 12 carbon atoms).

Examples of the compound to be used for introducing an amino group as the functional group include, for example, an amino acid.

The foregoing compound forms an amide bond by condensing the carboxyl group with the amino group in the electrostatic layer.

Among the foregoing compounds, the polyvalent carboxylic acid such as polyacrylic acid, polymethacrylic acid, trimellitic acid or butanetetracarboxylic acid can be also used for improving hydrophilicity.

On the solid support of the present invention, either of the nucleic acid molecules, DNA and RNA, can be immobilized. The number of bases in DNA or RNA is generally 1 to 200, preferably 5 to 150. In addition, in the case of DNA, either a single-stranded or double-stranded chain can be immobilized.

The solid support of the present invention can be used for an extension reaction of a nucleic acid molecule such as DNA. In this case, first a primer is immobilized on the solid support, and then a single-stranded or double-stranded DNA is hybridized. Thereafter, DNA complementary to the DNA hybridized to the primer is extended by a DNA extension reaction.

As the primer, a single-stranded or double-stranded nucleic acid molecule whose length and sequence are known is used. The length is not particularly limited, however, it is preferably 5 to 200 bases, more preferably 10 to 100 bases. The method of immobilizing the primer is not particularly limited, however, for example, a primer solution is prepared by dissolving a nucleic acid molecule in a buffer and the solid support of the present invention is dipped in the solution, whereby the primer can be immobilized on the surface of the solid support. The primer can be immobilized by performing dipping at generally 0 to 98° C., preferably 4 to 50° C. for generally 1 minute to 24 hours, preferably 10 minutes to 1 hour. In this case, by washing the solid support after dipping it for a predetermined period of time, the primer that is not immobilized can be removed. In addition, by using an apparatus called spotter, a wide variety of primer solutions can be immobilized on the surface of the solid support. In the case of using the spotter, for example, after primer solutions are spotted on the solid support with a spotter, baking is performed in a heated oven for a predetermined period of time, thereafter the washinging is performed, whereby the primer that is not immobilized is removed. By using a spotter, a wide variety of primers can be immobilized at different regions on the solid support, whereby a large number of assays can be carried out at one time, therefore it is advantageous in the field of detecting nucleic acids, which requires enormous assays.

In the conventional solid support, the primer is detached by a heat treatment in an extension reaction in some cases. On the other hand, in the solid support of the present invention, the primer is not detached even if heat is applied, and an extension reaction can be carried out in the state in which the primer has been immobilized on the solid support.

During this extension reaction, a labeled nucleic acid is allowed to be incorporated, and after the extension reaction, by reading a signal derived from the label, it can be detected whether or not a specific DNA has been hybridized to the primer and the extension reaction has progressed. Therefore, it can be determined whether DNA, which can be hybridized to the primer immobilized on the support, is contained in the tested sample. Therefore, it can be a useful detection means in research and medical practices.

The label is not particularly limited as long as it can be incorporated into a nucleic acid molecule, however, examples include a fluorescent label (CyDye such as Cy3 and Cy5, FITC, RITC, Rhodamine, TexasRed, TET, TAMRA, FAM, HEX, ROX and the like), a radiolabel ($\alpha\text{-}^{32}P$, $\gamma\text{-}^{32}P$, $^{35}S$ and the like) etc. In the case of using the fluorescence-labeled nucleic acid, it can be detected by making a fluorescent photograph of the solid support after the extension reaction.

The solid support of the present invention can be used in DNA amplification reaction. In the case of amplifying it by PCR reaction, for example, first a forward primer is immobilized on the solid support, a single-stranded or double-stranded DNA is hybridized, and then a complementary strand DNA is extended by an enzymatic reaction. Further, by carrying out the steps of (1) annealing, (2) hybridization and (3) extension reaction continuously, so-called PCR reaction progresses.

In the conventional solid support, there was a problem that the primer is detached by a heat treatment in PCR reaction or the control of thermal cycle could not be carried out well. However, in the solid support of the present invention, the primer is not detached even if heat is applied. Further, since the reaction is carried out not in a container, but in the state in which DNA has been immobilized on the solid support, the temperature in PCR reaction can be accurately controlled, and there is little possibility to affect the accuracy of the nucleotide sequence to be amplified, or to replicate DNA other than the target, therefore, DNA can be amplified efficiently.

In the case of using the solid support of the present invention for DNA amplification by the foregoing PCR, it is preferred that the thermal conductivity of the solid support be 0.1 W/cm·K or higher, more preferably 0.5 W/cm·K or higher, most preferably 1 W/cm·K or higher. It is based on the fact that if the thermal conductivity of the solid support is high, the following property for heating and cooling is superior in the case of carrying out PCR reaction or the like.

Specifically, it is preferred that as the substrate for producing the solid support, in terms of the thermal conductivity, diamond or the one coated with diamond or the like as the surface-treated layer on a variety of substrates be used.

Further, by combining the foregoing detection using the labeled nucleic acid with amplification by PCR, even in the case where only a small amount of DNA which can be hybridized to the primer on the solid support is contained in a sample, DNA is replicated as described above. As a result, a large amount of DNA is hybridized to the primer on the solid support, and the complementary strand is extended, whereby the detection sensitivity can be enhanced.

Alternatively, as the enzyme to be used for the extension reaction, a strand-displacing DNA polymerase is selected and a reverse primer is added, whereby DNA can be amplified on the solid support at a constant temperature without undergoing the thermal cycle. The strand-displacing DNA polymerase is a DNA synthase that can synthesize the complementary strand continuously by dissociating the double-stranded region if the double-stranded region is present in the extending direction during the process of synthesizing a DNA strand complementary to a template DNA.

The strand-displacing DNA polymerase is not particularly limited, however, examples include, for example, BCA BEST DNA polymerase (Takara Bio), Phi29 DNA polymerase (Amersham Bioscience) and the like.

In another embodiment of the present invention, by using cDNA synthesized from mRNA as a target, RNA, though it is indirect, can also become a target.

In this case, cDNA is obtained from mRNA by utilizing a reverse transcription reaction, however, cDNA can be immobilized on the solid support at the same time when it is obtained. First, a reverse transcription primer is bound to the chemically modified region of the solid support. As the primer, an oligo dT primer, a primer complementary to a specific nucleotide sequence or a random 6-mer primer is generally used, however, in particular, it is desired to use an oligo dT primer comprising a sequence, in which there are about 10 to 20 Ts (thymines) in a row, corresponding to the poly(A)+ sequence at the 5'-terminus of RNA.

In the case of using the oligo dT primer, the poly(A) region at the 5'-terminus of RNA to be used as the template is annealed. A reverse transcriptase is allowed to act on this, and dNTP complementary to the template RNA is polymerized at the 3'-terminus of the primer one after another, whereby cDNA is synthesized in the direction from the 5' to the 3'. The binding of primer, annealing, and polymerization of a complementary strand by a reverse transcriptase in this reverse transcription reaction can be carried out by controlling the temperature (thermal cycle) according to the usual methods.

As described above, immobilization on the solid support can be carried out at the same time when reverse transcription reaction is carried out, therefore, according to the method of the present invention, so-called RT-PCR (reverse transcript-PCR) can be efficiently carried out. Therefore, the present invention is also useful for quantifying mRNA.

Further, by immobilizing the terminal base of an oligonucleotide on a terminal hydroxyl group or terminal carboxyl group through a hydrogen bond with the use of the support of the present invention, and further immobilizing DNA having a base sequence complementary to this oligonucleotide, the resultant product can be used as a DNA library chip. In addition, by immobilizing a nucleotide, oligonucleotide, DNA fragment or the like instead of DNA, the resultant product can be used as a library.

By performing the detection as described above with the use of the solid support of the present invention, diagnosis of a disease can be also performed.

EXAMPLES

Hereunder, the present invention will be explained with reference to the Examples, however, the present invention is not intended to be limited thereto.

Example 1

Introduction of Amino Group-containing Compound into Chamber when Applying Surface-treated Layer to Substrate (1)

DLC layer was formed at a thickness of 10 nm on a slide glass of 25 mm (width)×75 mm (length)×1 mm (thickness) by the ionization deposition method, at an accelerating voltage of 0.5 kV, using a mixed gas of 95% by volume of methane gas and 5% by volume of hydrogen gas as material. Then, using methane gas as a carrier gas, at the rate of 5 cm$^3$/minute, it was introduced into a chamber through the ethylenediamine incubated at 15° C. At a working pressure of 2 Pa and an accelerating voltage of 0.5 kV, using methane and ethylenediamine as material, a layer consisting of C, N and H was formed at a thickness of 10 nm.

Then, after butanetetracarboxylic acid anhydride, as a polyvalent carboxylic acid, was condensed with the amino group in the surface-treated layer consisting of C, N and H formed with methane and ethylenediamine as material, it was activated by being dipped in an activation solution, in which 0.1 M 1-[3-(dimethylamino)propyl]-3-ethylcarbodiimide and 20 mM N-hydroxysuccineimide had been dissolved in 300 mL of 0.1 M phosphate buffer (pH 6), for 30 minutes.

Then, About 1 nL of 500 bp Cy3-labeled double-stranded DNA, which had been amplified by PCR using lambda DNA prepared at a concentration of 0.1 μg/μL as a template, was spotted on the substrate using a microarray maker. Then, after it was heated in an oven at 80° C. for 3 hours and washed with 2×SSC/0.2% SDS, the intensity of fluorescence of the spotted DNA was measured.

As a result, the intensity of fluorescence was 36,050. Further, when the intensity of fluorescence was measured after performing washing with 2×SSC/0.2% SDS at 95° C., it was 35,540, which was hardly decreased at all.

As a comparison, after a slide glass was dipped in an ethanol solution containing 2% by weight of 3-aminoprolyl-triethoxysilane for 10 minutes, it was taken out, washed with ethanol, and dried at 110° C. for 10 minutes. Then, after succinic acid anhydride was condensed with this substrate to which an amino group was introduced, it was activated by being dipped in an activation solution, in which 0.1 M 1-[3-(dimethylamino)propyl]-3-ethylcarbodiimide and 20 mM N-hydroxysuccineimide had been dissolved in 300 mL of 0.1 M phosphate buffer (pH 6), for 30 minutes. After 500 bp Cy3-labeled double-stranded DNA, which had been amplified by PCR using lambda DNA as a template, was immobilized in the same manner on the thus obtained substrate, the substrate was washed with 2×SSC/0.2% SDS. As a result, the intensity of fluorescence was 23,500. Further, when the intensity of fluorescence was measured after performing washing with 2×SSC/0.2% SDS at 95° C., it was 23,000, which was hardly decreased at all.

In other word, by using a covalent bond type substrate that hardly has an electrostatic layer, although DNA can be immobilized more firmly by a covalent bond, the intensity of a fluorescence signal was not increased.

Further, after 500 bp Cy3-labeled double-stranded DNA, which had been amplified by PCR using lambda DNA as a template, was immobilized in the same manner on a substrate that does not have an electrostatic layer (after 5% polyacrylic acid aqueous solution was applied on a slide glass and dried, ultraviolet rays were irradiated for 60 minutes to make it insoluble. Then, it was activated by being dipped in an activation solution, in which 0.1 M 1-[3-(dimethylamino)propyl]-3-ethylcarbodiimide and 20 mM N-hydroxysuccineimide had been dissolved in 300 mL of 0.1 M phosphate buffer (pH 6), for 30 minutes), the substrate was washed with 2×SSC/0.2% SDS. As a result, though the polyacrylic acid layer was detached, the intensity of fluorescence was 26,220 in the region where the layer remained. Further, the polyacrylic acid layer was completely detached when being washed with 2×SSC/0.2% SDS at 95° C.

Example 2

Introduction of Amino Group-containing Compound into Chamber when Applying Surface-treated Layer to Substrate (2)

To a slide glass of 25 mm (width)×75 mm (length)×1 mm (thickness) by the ionization deposition method, using methane gas as a carrier gas, at the rate of 5 cm$^3$/minute, it was introduced into a chamber through the ethylenediamine incubated at 15° C. At a working pressure of 2 Pa and an accelerating voltage of 0.5 kV, using methane and ethylenediamine as material, a layer consisting of C, N and H was formed at a thickness of 20 nm.

Then, after polyacrylic acid, as a polyvalent carboxylic acid, was condensed with the amino group in the surface-treated layer consisting of methane and ethylenediamine in the presence of 0.1 M 1-[3-(dimethylamino)propyl]-3-ethylcarbodiimide, it was activated by being dipped in an activation solution, in which 0.1 M 1-[3-(dimethylamino)propyl]-3-ethylcarbodiimide and 20 mM N-hydroxysuccineimide had been dissolved in 300 mL of 0.1 M phosphate buffer (pH 6), for 30 minutes.

Then, about 1 nL of 500 bp Cy3-labeled double-stranded DNA, which had been amplified by PCR using lambda DNA prepared at a concentration of 0.1 µg/µL as a template, was spotted on the substrate using a microarray maker. Then, after it was heated in an oven at 80° C. for 3 hours and washed with 2×SSC/0.2% SDS, the intensity of fluorescence of the spotted DNA was measured.

As a result, the intensity of fluorescence was 34,050. Further, when the intensity of fluorescence was measured after performing washing with 2×SSC/0.2% SDS at 95° C., it was 33,500, which was hardly decreased at all.

As a comparison, after 500 bp Cy3-labeled double-stranded DNA, which had been amplified by PCR using lambda DNA as a template, was immobilized in the same manner on a commercially available electrostatic type substrate (manufactured by Matsunami Glass Ind., LTD.; a substrate which is a slide glass applied with aminosilane (a silane coupling agent)), the substrate was washed with 2×SSC/0.2% SDS. As a result, the intensity of fluorescence was 35,460. Further, when the intensity of fluorescence was measured after performing washing with 2×SSC/0.2% SDS at 95° C., it was decreased to 26,210.

Further, after 500 bp Cy3-labeled double-stranded DNA, which had been amplified by PCR using lambda DNA as a template, was immobilized in the same manner on a substrate that does not have an electrostatic layer (after 5% polyacrylic acid aqueous solution was applied on a slide glass and dried, ultraviolet rays were irradiated for 60 minutes to make it insoluble. Then, it was activated by being dipped in an activation solution, in which 0.1 M 1-[3-(dimethylamino)propyl]-3-ethylcarbodiimide and 20 mM N-hydroxysuccineimide had been dissolved in 300 mL of 0.1 M phosphate buffer (pH 6), for 30 minutes), the substrate was washed with 2×SSC/0.2% SDS. As a result, though the polyacrylic acid layer was detached, the intensity of fluorescence was 26,220 in the region where the layer remained. Further, the polyacrylic acid layer was completely detached when being washed with 2×SSC/0.2% SDS at 95° C.

Example 3

Formation of Electrostatic Layer by Post-treatment

DLC layer was formed at a thickness of 10 nm on a slide glass of 25 mm (width)×75 mm (length)×1 mm (thickness) by the ionization deposition method, at an accelerating voltage of 0.5 kV, using a mixed gas of 95% by volume of methane gas and 5% by volume of hydrogen gas as material.

Then, it was chlorinated by being irradiated with ultraviolet rays for 30 minutes in chlorine gas. Then, the substrate was dipped in a polyacrylic amine aqueous solution (0.1 g/L), whereby an electrostatic layer was formed.

Then, after polyacrylic acid, as a polyvalent carboxylic acid, was condensed with the amino group in the electrostatic layer in the presence of 0.1 M 1-[3-(dimethylamino)propyl]-3-ethylcarbodiimide, it was activated by being dipped in an activation solution, in which 0.1 M 1-[3-(dimethylamino)propyl]-3-ethylcarbodiimide and 20 mM N-hydroxysuccineimide had been dissolved in 300 mL of 0.1 M phosphate buffer (pH 6), for 30 minutes.

Then, about 1 nL of 500 bp Cy3-labeled double-stranded DNA, which had been amplified by PCR using lambda DNA prepared at a concentration of 0.1 µg/µL as a template, was spotted on the substrate using a microarray maker. Then, after it was heated in an oven at 80° C. for 3 hours and washed with 2×SSC/0.2% SDS, the intensity of fluorescence of the spotted DNA was measured.

As a result, the intensity of fluorescence was 35,000. Further, when the intensity of fluorescence was measured after performing washing with 2×SSC/0.2% SDS at 95° C., it was 34,500, which was hardly decreased at all.

As a comparison, after 5% polyacrylic acid aqueous solution was applied to a slide glass on which DLC was formed at a thickness of 10 nm and dried, ultraviolet rays were irradiated for 60 minutes to make it insoluble. Then, it was activated by being dipped in an activation solution, in which 0.1 M 1-[3-(dimethylamino)propyl]-3-ethylcarbodiimide and 20 mM N-hydroxysuccineimide had been dissolved in 300 mL of 0.1 M phosphate buffer (pH 6), for 30 minutes. After 500 bp Cy3-labeled double-stranded DNA, which had been amplified by PCR using lambda DNA as a template was immobilized in the same manner, and washed with 2×SSC/0.2% SDS, the polyacrylic acid layer was completely detached.

Example 4

Immobilization of Primer by Dipping Method

DLC layer was formed at a thickness of 100 nm on an Si substrate cut into 3 mm square by the ionization deposition method, at an accelerating voltage of 0.5 kV, using a mixed gas of 95% by volume of methane gas and 5% by volume of hydrogen gas as material. Then, methane gas and hydrogen gas were replaced with ammonia gas atmosphere and aminization was carried out for 10 minutes by the plasma method.

Then, after a polyvalent carboxylic acid (polyacrylic acid) was condensed with the amino group introduced in the surface-treated layer, it was activated by being dipped in an activation solution, in which 0.1 M 1-[3-(dimethylamino)propyl]-3-ethylcarbodiimide and 20 mM N-hydroxysuccineimide had been dissolved in 0.1 M phosphate buffer (pH 6), for 30 minutes.

Then, the immobilization reaction was carried out by dipping the solid support at room temperature for 1 hour in a solution of a forward primer (22 bases) of the 500 bp lambda DNA prepared at a concentration of 0.1 µg/µL using sterile water. After the reaction, the solid support was washed with a washing solution (2×SSC/0.2% SDS) twice and rinsed with sterile water.

The solid support, on which the forward primer had been immobilized, was dipped in a solution of the 500 bp lambda DNA that is complementary to the immobilized primer (0.025 µg/µL, buffer: 5×SSC/0.5% SDS/20% formamide). After it was incubated at 98° C. for 5 minutes, it was incubated at 42° C. for 12 hours. After the reaction, the solid support was washed with a washing solution (2×SSC/0.2% SDS) twice and rinsed with sterile water.

The solid support after hybridization was dipped in a reaction solution (1×Exbuffer/0.025 mM Cy3-dCTP/1.25 mM dNTP/0.25 U ExTaq) and incubated at 42° C. for 6 hours. After the reaction, the solid support was washed with a washing solution (2×SSC/0.2% SDS) twice and rinsed with sterile water.

When the solid support after the washing was observed with a fluorescence image scanner, a fluorescence signal by the extension reaction was detected.

Example 5

Immobilization of Primer by Spotting Method (1)

DLC layer was formed at a thickness of 100 nm on an Si substrate cut into 3 mm square by the ionization deposition method, at an accelerating voltage of 0.5 kV, using a mixed gas of 95% by volume of methane gas and 5% by volume of hydrogen gas as material. Then, methane gas and hydrogen gas were replaced with ammonia gas atmosphere and aminization was carried out for 10 minutes by the plasma method.

Then, after a polyvalent carboxylic acid (polyacrylic acid) was condensed with the amino group introduced in the surface-treated layer, it was activated by being dipped in an activation solution, in which 0.1 M 1-[3-(dimethylamino)propyl]-3-ethylcarbodiimide and 20 mM N-hydroxysuccinimide had been dissolved in 0.1 M phosphate buffer (pH 6), for 30 minutes.

Then, solutions of forward primers (22 bases, 10 samples) of the 500 bp lambda DNA prepared at a concentration of 0.1 μg/μL using 20% DMSO solution were spotted on the solid support by using a spotter. Then, after being placed in an oven heated at 80° C. for 1 hour, it was washed with a washing solution (2×SSC/0.2% SDS) twice and rinsed with sterile water.

The solid support, on which the primers had been immobilized, was dipped in a solution of the single-stranded 500 bp lambda DNA that is complementary to the immobilized primers (0.025 μg/μL, buffer: 5×SSC/0.5% SDS/20% formamide) After it was incubated at 98° C. for 5 minutes, it was incubated at 42° C. for 12 hours. After the reaction, the solid support was washed with a washing solution (2×SSC/0.2% SDS) twice and rinsed with sterile water.

The solid support after hybridization was dipped in a reaction solution (1×Exbuffer/0.025 mM Cy3-dCTP/1.25 mM dNTP/0.25 U ExTaq) and incubated at 42° C. for 6 hours. After the reaction, the solid support was washed with a washing solution (2×SSC/0.2% SDS) twice and rinsed with sterile water.

When the solid support after the washing was observed with a fluorescence image scanner, a fluorescence signal by the extension reaction was detected.

Example 6

Immobilization of Primer by Spotting Method (2)

DLC layer was formed at a thickness of 10 nm on a slide glass of 25 mm (width)×75 mm (length)×1 mm (thickness) by the ionization deposition method, at an accelerating voltage of 0.5 kV, using a mixed gas of 95% by volume of methane gas and 5% by volume of hydrogen gas as material. Then, methane gas and hydrogen gas were replaced with ammonia gas atmosphere and aminization was carried out for 10 minutes by the plasma method.

Then, after a polyvalent carboxylic acid (polyacrylic acid) was condensed with the amino group introduced in the surface-treated layer, it was activated by being dipped in an activation solution, in which 0.1 M 1-[3-(dimethylamino)propyl]-3-ethylcarbodiimide and 20 mM N-hydroxysuccinimide had been dissolved in 0.1 M phosphate buffer (pH 6), for 30 minutes.

Then, solutions of forward primers (22 bases, 10 samples) of the 500 bp lambda DNA prepared at a concentration of 0.1 μg/μL using 20% DMSO solution were spotted on the solid support by using a spotter. Then, after being placed in an oven heated at 80° C. for 1 hour, it was washed with a washing solution (2×SSC/0.2% SDS) twice and rinsed with sterile water.

On the solid support, 15 μL of a solution of the 500 bp lambda DNA that is complementary to the immobilized primers (0.025 μg/μL, buffer: 5×SSC/0.5% SDS/20% formamide) was placed and further overlaid with a cover glass. After hybridization was carried out by incubating at 42° C. for 5 hours, the cover glass was washed out with 0.1×SSC and the solid support was washed with a washing solution (2×SSC/0.2% SDS) twice and rinsed with sterile water.

After hybridization, on the solid support, 15 μL of a reaction solution (1×Exbuffer/0.025 mM Cy3-dCTP/1.25 mM dNTP/0.25 U ExTaq) was placed and further overlaid with a cover glass. After an extension reaction was carried out by incubating at 42° C. for 5 hours, the cover glass was washed out with 0.1×SSC and the solid support was washed with a washing solution (2×SSC/0.2% SDS) twice and rinsed with sterile water.

When the solid support after the washing was observed with a fluorescence image scanner, a fluorescence signal by the extension reaction was detected.

Example 7

Annealing, Hybridization, Extension Reaction

DLC layer was formed at a thickness of 100 nm on an Si substrate cut into 3 mm square by the ionization deposition method, at an accelerating voltage of 0.5 kV, using a mixed gas of 95% by volume of methane gas and 5% by volume of hydrogen gas as material. Then, methane gas and hydrogen gas were replaced with ammonia gas atmosphere and aminization was carried out for 10 minutes by the plasma method.

Then, after a polyvalent carboxylic acid (polyacrylic acid) was condensed with the amino group introduced in the surface-treated layer, it was activated by being dipped in an activation solution, in which 0.1 M 1-[3-(dimethylamino)propyl]-3-ethylcarbodiimide and 20 mM N-hydroxysuccinimide had been dissolved in 0.1 M phosphate buffer (pH 6), for 30 minutes.

Then, solutions of forward primers (22 bases, 10 samples) of the 500 bp lambda DNA prepared at a concentration of 0.1 μg/μL using 20% DMSO solution were spotted on the solid support by using a spotter. Then, after being placed in an oven heated at 80° C. for 1 hour, it was washed with a washing solution (2×SSC/0.2% SDS) twice and rinsed with sterile water.

The 500 bp lambda DNA, which was complementary to one of the immobilized primers, was added to a reaction solution (1×Exbuffer/0.025 mM Cy3-dCTP/1.25 mM dNTP/0.25 U ExTaq) to give a final concentration of 0.025 μg/μL.

The reaction solution was placed in a PCR tube and further a reverse primer was added. The solid support, on which the primers had been immobilized, was dipped in the reaction solution and a cycle consisting of annealing (94° C., 1 minute), hybridization (60° C., 1 minute) and extension reaction (72° C., 1 minute) was repeated 30 times. After the reaction, the solid support was washed with a washing solution (2×SSC/0.2% SDS) twice and rinsed with sterile water.

When the solid support after the washing was observed with a fluorescence image scanner, a more intense fluorescence signal was detected than in the case where the reaction was carried out at a constant temperature.

Further, when the solid support, with which the extension reaction had been carried out, was put in a PCR reaction solution and PCR reaction was carried out to amplify the 500 bp lambda DNA, the amplification of 500 bp region was confirmed by electrophoresis.

Example 8

Amplification Reaction Using Strand-displacing DNA Polymerase

DLC layer was formed at a thickness of 100 nm on an Si substrate cut into 3 mm square by the ionization deposition method, at an accelerating voltage of 0.5 kV, using a mixed gas of 95% by volume of methane gas and 5% by volume of hydrogen gas as material. Then, methane gas and hydrogen gas were replaced with ammonia gas atmosphere and aminization was carried out for 10 minutes by the plasma method.

Then, after a polyvalent carboxylic acid (polyacrylic acid) was condensed with the amino group introduced in the surface-treated layer, it was activated by being dipped in an activation solution, in which 0.1 M 1-[3-(dimethylamino)propyl]-3-ethylcarbodiimide and 20 mM N-hydroxysuccineimide had been dissolved in 0.1 M phosphate buffer (pH 6), for 30 minutes.

Then, solutions of forward primers (22 bases, 10 samples) of the 500 bp lambda DNA prepared at a concentration of 0.1 µg/µL using 20% DMSO solution were spotted on the solid support by using a spotter. Then, after being placed in an oven heated at 80° C. for 1 hour, it was washed with a washing solution (2×SSC/0.2% SDS) twice and rinsed with sterile water.

The solid support, on which the primers had been immobilized, was dipped in a solution of the 500 bp lambda DNA that is complementary to the immobilized primers (0.025 µg/µL, buffer: 5×SSC/0.5% SDS/20% formamide). After it was incubated at 98° C. for 5 minutes, it was incubated at 42° C. for 12 hours. After the reaction, the solid support was washed with a washing solution (2×SSC/0.2% SDS) twice and rinsed with sterile water.

The solid support after hybridization was dipped in a reaction solution (BcaBEST DNA polymerase/20 mM Tris/10 mM $MgCl_2$), to which a reverse primer had been added, and was incubated at 60° C. for 6 hours. After the reaction, the solid support was washed with a washing solution (2×SSC/0.2% SDS) twice and rinsed with sterile water. The enzyme used is a strand-displacing DNA polymerase (manufactured by TAKARA).

When the solid support after the washing was observed with a fluorescence image scanner, a fluorescence signal by the extension reaction was detected.

Further, when the solid support, with which the extension reaction had been carried out, was put in a PCR reaction solution and PCR reaction was carried out to amplify the 500 bp lambda DNA, the amplification of 500 bp region was confirmed by electrophoresis.

Example 9

Annealing, Hybridization, Extension Reaction (2)

DLC layer was formed at a thickness of 100 nm on an Si substrate cut into 3 mm square by the ionization deposition method, at an accelerating voltage of 0.5 kV, using a mixed gas of 95% by volume of methane gas and 5% by volume of hydrogen gas as material. Then, methane gas and hydrogen gas were replaced with ammonia gas atmosphere and aminization was carried out for 10 minutes by the plasma method.

Then, after a polyvalent carboxylic acid (polyacrylic acid) was condensed with the amino group introduced in the surface-treated layer, it was activated by being dipped in an activation solution, in which 0.1 M 1-[3-(dimethylamino)propyl]-3-ethylcarbodiimide and 20 mM N-hydroxysuccineimide had been dissolved in 0.1 M phosphate buffer (pH 6), for 30 minutes.

Then, a 0.1 µg/µL forward primer solution (5'-GATGAGT-TGTGTCCGTACAACT-3' (see the sequence number 1 in the sequence table), 22bases, 20% DMSO), a 0.1 µg/µL reverse primer solution (5'-GGTTATCGAAATCAGCCA-CAGCGCC-3' (see the sequence number 2 in the sequence table), 20% DMSO) and a 0.05 µg/µL forward+reverse primer solution (20% DMSO) were spotted on the solid support by using a spotter. Then, after being placed in an oven heated at 80° C. for 1 hour, it was washed with a washing solution (2×SSC/0.2% SDS) twice and rinsed with sterile water.

Reaction solution 1 (0.025 µg/µL lambda DNA/1 pmol/µL reverse primer/1×Exbuffer/0.025 mM Cy3-dCTP/1.25 mM dNTP/0.25U ExTaq) was placed in a PCR tube and the solid support, on which the primers had been immobilized, was dipped in the reaction solution and a cycle consisting of annealing (94° C., 30 seconds), hybridization and extension reaction (68° C., 30 seconds) was repeated 30 times. After the reaction, the solid support was washed with a washing solution (2×SSC/0.2% SDS) twice and rinsed with sterile water.

When the solid support after the washing was observed with a fluorescence image scanner, a more intense fluorescence signal was detected than in the case where the reaction was carried out at a constant temperature.

Further, when the solid support, with which the extension reaction had been carried out, was put in reaction solution 2 (1 pmol/µL forward primer/1 pmol/µL reverse primer/1×Exbuffer/1.25 mM dNTP/0.25 U ExTaq) and a cycle consisting of annealing (94° C., 30 seconds), hybridization and extension reaction (68° C., 30 seconds) was repeated 30 times, the amplification of DNA fragment in the 500 bp region was confirmed by electrophoresis.

Example 10

Immobilization of Primer by Dipping Method (2)

After a glass substrate cut into 3 mm square was dipped in a polyacrylic amine aqueous solution adjusted to 0.1% and a polyvalent carboxylic acid (polyacrylic acid) was condensed with the amino group introduced in the substrate surface, it was activated by being dipped in an activation solution, in which 0.1 M 1-[3-(dimethylamino)propyl]-3-ethylcarbodiimide and 20 mM N-hydroxysuccineimide had been dissolved in 0.1 M phosphate buffer (pH 6), for 30 minutes.

Then, the immobilization reaction was carried out by dipping the solid support at room temperature for 1 hour in a solution of a forward primer (22 bases) of the 500 bp lambda DNA prepared at a concentration of 0.1 µg/µL using sterile water. After the reaction, the solid support was washed with a washing solution (2×SSC/0.2% SDS) twice and rinsed with sterile water.

The solid support, on which the forward primer had been immobilized, was dipped in a solution of the 500 bp lambda DNA that is complementary to the immobilized primer (0.025 µg/µL, buffer: 5×SSC/0.5% SDS/20% formamide). After it was incubated at 98° C. for 5 minutes, it was incubated at 42° C. for 12 hours. After the reaction, the solid support was washed with a washing solution (2×SSC/0.2% SDS) twice and rinsed with sterile water.

The solid support after hybridization was dipped in a reaction solution (1×Exbuffer/0.025 mM Cy3-dCTP/1.25 mM dNTP/0.25 U ExTaq) and incubated at 42° C. for 6 hours. After the reaction, the solid support was washed with a washing solution (2×SSC/0.2% SDS) twice and rinsed with sterile water.

When the solid support after the washing was observed with a fluorescence image scanner, a fluorescence signal by the extension reaction was detected.

Comparative Example

After a glass substrate cut into 3 mm square was dipped in a 3-aminopropyltriethoxysilane solution adjusted at a concentration of 4% with 95% ethanol, the surface was aminized by baking it in an oven at 100° C. for 20 minutes.

Then, by dipping the substrate at room temperature for 1 hour in a solution of a forward primer (22 bases) of the 500 bp lambda DNA prepared at a concentration of 0.1 μg/μL using sterile water, the immobilization reaction by electrostatic binding was carried out. After the reaction, the substrate was washed with a washing solution (2×SSC/0.2% SDS) twice and rinsed with sterile water. In addition, a substrate that had been dipped in a solution of a fluorescence-labeled forward primer (22 bases) of the 500 bp lambda DNA was also prepared.

The substrate, on which the forward primer had been immobilized, was dipped in a solution of the 500 bp lambda DNA that is complementary to the immobilized primer (0.025 μg/μL, buffer: 5×SSC/0.5% SDS/20% formamide). After it was incubated at 98° C. for 5 minutes, it was incubated at 42° C. for 12 hours. After the reaction, the substrate was washed with a washing solution (2×SSC/0.2% SDS) twice and rinsed with sterile water.

The substrate after hybridization was dipped in a reaction solution (1×Exbuffer/0.025 mM Cy3-dCTP/1.25 mM dNTP/0.25 U ExTaq) and incubated at 42° C. for 6 hours. After the reaction, the substrate was washed with a washing solution (2×SSC/0.2% SDS) twice and rinsed with sterile water.

When the substrate after the washing was observed with a fluorescence image scanner, a fluorescence signal by the extension reaction was not detected at all.

With regard to the substrate to which the fluorescence-labeled forward primer solution (22 bases) of the 500 bp lambda DNA had been immobilized, although a faint fluorescence signal was observed after the immobilization reaction, a fluorescence signal was not detected at all in the observation of a fluorescence image after the same procedure was carried out. This indicates that the primer immobilized on the substrate was detached during the procedure.

The intensities of fluorescence measured with a fluorescence image scanner in the foregoing Examples 4 to 10 are summarized in the following Table 1.

TABLE 1

Intensities of Fluorescence Signal in Examples 4 to 10

| Example | Intensity of Fluorescence Signal | | |
|---|---|---|---|
| | Before reaction | Spot A | Spot B |
| 4 | 4500 | 9000 | — |
| 5 | 4500 | 9500 | 11000 |
| 6 | 2500 | 6000 | 7500 |
| 7 | 4500 | 21000 | 22500 |
| 8 | 4500 | 15500 | 16000 |
| 9 | 4500 | 20000 | 22000 |
| 10 | 2000 | 7000 | — |

Industrial Applicability

On the solid support of the present invention, a larger amount of nucleic acid molecules can be immobilized than on the conventional solid support, and it can be immobilized firmly through a covalent bond. Therefore, the detection sensitivity and reliability that were the problems of the conventional DNA array can be improved. Further, since an extension reaction can be performed in the state in which a nucleic acid molecule has been immobilized, or a nucleic acid molecule can be amplified by performing PCR reaction, it is possible to aim at generalizing a DNA array.

The invention claimed is:

1. A solid support comprising:
   a. a substrate;
   b. an electrostatic layer comprising a positively charged compound on the substrate, wherein the electrostatic layer is formed by a polymer, and the electrostatic layer includes an amino group-containing compound that is polyallylamine;
   c. a surface-treated layer comprising diamond between the substrate and the electrostatic layer,
   d. a chemically modifying layer comprising a carboxyl group on the electrostatic layer for introducing a functional group for covalently binding to a nucleic acid molecule, wherein said chemically modifying layer is a polyvalent carboxylic acid, and wherein the polyvalent carboxylic acid is a polyacrylic acid; and
   e. a nucleic acid molecule bonded covalently to the chemically modifying layer.

2. The solid support according to claim 1, wherein the electrostatic layer includes an amino group-containing compound that does not covalently bond to the substrate.

3. The solid support according to claim 1, wherein the electrostatic layer includes an amino group-containing compound by covalently binding to the substrate, and the compound containing an amino group has an amino group at the terminus to which the substrate does not bind.

4. The solid support according to claim 1, wherein the electrostatic layer has a thickness of from 1 nm to 500 microns.

5. The solid support according to claim 1, wherein the nucleic acid molecule is immobilized as a spot.

6. The solid support according to claim 1, wherein the diamond is a soft diamond that is diamond-like carbon.

7. The solid support according to claim 1, wherein the nucleic acid is covalently bound to the carboxyl group.

8. The solid support according to claim 1 wherein the thickness of the surface-treated layer has a thickness of from 1 nm to 100 nm.

9. The solid support according to claim 1, wherein a reflective layer is formed on a surface of the substrate.

10. The solid support according to claim 1, wherein a thermal conductivity of the solid support is 0.1 W/cm.K or more.

* * * * *